(12) United States Patent
Muller et al.

(10) Patent No.: US 11,273,115 B2
(45) Date of Patent: *Mar. 15, 2022

(54) HAIR DYEING METHOD USING A DYE COMPOSITION AND AN OXIDIZING COMPOSITION, SAID COMPOSITIONS COMPRISING A SCLEROGLUCAN GUM

(71) Applicant: L'OREAL, Paris (FR)

(72) Inventors: Sabrina Muller, Saint-Ouen (FR); Delphine Charrier, Saint-Ouen (FR); Aldo Pizzino, Saint-Ouen (FR); Frédéric Simonet, Saint-Ouen (FR); Mladen Milic, Saint-Ouen (FR); Cindy Yadel, Saint-Ouen (FR); Fanny Cardonnel, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/253,007

(22) PCT Filed: Jun. 20, 2019

(86) PCT No.: PCT/EP2019/066364
§ 371 (c)(1),
(2) Date: Dec. 16, 2020

(87) PCT Pub. No.: WO2019/243508
PCT Pub. Date: Dec. 26, 2019

(65) Prior Publication Data
US 2021/0113449 A1 Apr. 22, 2021

(30) Foreign Application Priority Data
Jun. 20, 2018 (FR) ...................... 1855429

(51) Int. Cl.
| | |
|---|---|
| A61Q 5/10 | (2006.01) |
| A61K 8/73 | (2006.01) |
| A45D 19/00 | (2006.01) |
| A45D 34/00 | (2006.01) |
| A61K 8/19 | (2006.01) |
| A61K 8/22 | (2006.01) |
| A61K 8/25 | (2006.01) |
| A61K 8/31 | (2006.01) |
| A61K 8/34 | (2006.01) |
| A61K 8/41 | (2006.01) |
| A61K 8/60 | (2006.01) |
| A61K 8/88 | (2006.01) |

(52) U.S. Cl.
CPC ............ *A61K 8/73* (2013.01); *A45D 19/0066* (2021.01); *A45D 34/00* (2013.01); *A61K 8/19* (2013.01); *A61K 8/22* (2013.01); *A61K 8/25* (2013.01); *A61K 8/31* (2013.01); *A61K 8/342* (2013.01); *A61K 8/347* (2013.01); *A61K 8/41* (2013.01); *A61K 8/415* (2013.01); *A61K 8/604* (2013.01); *A61K 8/88* (2013.01); *A61Q 5/10* (2013.01); *A61K 2800/4322* (2013.01); *A61K 2800/4324* (2013.01); *A61K 2800/87* (2013.01); *A61K 2800/882* (2013.01)

(58) Field of Classification Search
CPC . A61Q 5/10; A61K 8/22; A61K 8/415; A61K 8/19; A61K 2800/4324; A61K 8/41; A61K 8/342; A61K 2800/882; A61K 8/347; A61K 8/602; A61K 2800/4322; A61K 2800/87; A45D 19/0066
USPC .......................................................... 8/405
See application file for complete search history.

(56) References Cited

U.S. PATENT DOCUMENTS

| | | | |
|---|---|---|---|
| 2,261,002 | A | 10/1941 | Ritter |
| 2,271,378 | A | 1/1942 | Searle |
| 2,273,780 | A | 2/1942 | Dittmar |
| 2,375,853 | A | 5/1945 | Kirby et al. |
| 2,388,614 | A | 11/1945 | Kirby et al. |
| 2,454,547 | A | 11/1948 | Bock et al. |

(Continued)

FOREIGN PATENT DOCUMENTS

| | | |
|---|---|---|
| DE | 2359399 A1 | 6/1975 |
| DE | 3843892 A1 | 6/1990 |

(Continued)

OTHER PUBLICATIONS

International Search Report and Written Opinion for counterpart Application No. PCT/EP2019/066365, dated Aug. 13, 2019.

(Continued)

*Primary Examiner* — Eisa B Elhilo
(74) *Attorney, Agent, or Firm* — The Marbury Law Group, PLLC

(57) ABSTRACT

The disclosure relates to a method for dyeing keratin fibers, in particular human keratin fibers such as hair, involving the application of a dye composition (A) on the fibers, said dye composition comprising one or more oxidation dyes, one or more scleroglucan gums in a total weight content greater than or equal to 0.5% relative to the total weight of the composition (A) and one or more alkaline agents, and the application of an oxidizing composition (B) comprising one or more chemical oxidizing agents and one or more scleroglucan gums preferably in a total weight content greater than or equal to 0.5% relative to the total weight of the composition (B); the oxidizing composition (B) being mixed with the dye composition (A) just before use (application on said fibers). The disclosure also relates to a multi-compartment device suitable for implementing the method.

20 Claims, No Drawings

(56) References Cited

U.S. PATENT DOCUMENTS

| | | |
|---|---|---|
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,589,978 A | 6/1971 | Kamal et al. |
| 3,632,559 A | 1/1972 | Matter et al. |
| 3,874,870 A | 4/1975 | Green et al. |
| 3,910,862 A | 10/1975 | Barabas et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 4,001,432 A | 1/1977 | Green et al. |
| 4,005,193 A | 1/1977 | Green et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,137,180 A | 1/1979 | Naik et al. |
| 4,157,388 A | 6/1979 | Christiansen |
| 4,165,367 A | 8/1979 | Chakrabarti |
| 4,172,887 A | 10/1979 | Vanlerberghe et al. |
| 4,217,914 A | 8/1980 | Jacquet et al. |
| 4,240,450 A | 12/1980 | Grollier et al. |
| 4,349,532 A | 9/1982 | Vanlerberghe et al. |
| 4,381,919 A | 5/1983 | Jacquet et al. |
| 4,591,610 A | 5/1986 | Grollier |
| 4,702,906 A | 10/1987 | Jacquet et al. |
| 4,719,282 A | 1/1988 | Nadolsky et al. |
| 4,761,273 A | 8/1988 | Grollier et al. |
| 4,839,166 A | 6/1989 | Grollier et al. |
| 4,874,554 A | 10/1989 | Lange et al. |
| 4,996,059 A | 2/1991 | Grollier et al. |
| 5,061,289 A | 10/1991 | Clausen et al. |
| 5,089,252 A | 2/1992 | Grollier et al. |
| 5,180,397 A * | 1/1993 | Grollier .............. A61K 8/20 8/405 |
| 5,180,399 A * | 1/1993 | Grollier .............. A61K 8/20 8/405 |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,766,576 A | 6/1998 | Löwe et al. |
| 6,099,592 A | 8/2000 | Vidal et al. |
| 2003/0229948 A1* | 12/2003 | Desenne .............. A61Q 5/10 8/405 |
| 2004/0034946 A1 | 2/2004 | Legrand et al. |
| 2004/0060125 A1 | 4/2004 | Audouset |
| 2004/0064901 A1 | 4/2004 | Kleen et al. |
| 2004/0133993 A1 | 7/2004 | Cottard et al. |
| 2004/0172771 A1 | 9/2004 | Cottard et al. |
| 2004/0221401 A1 | 11/2004 | Desenne et al. |
| 2005/0039270 A1 | 2/2005 | Legrand et al. |
| 2006/0117493 A1 | 6/2006 | Bureiko et al. |
| 2006/0182697 A1 | 8/2006 | Lalleman et al. |
| 2008/0282481 A1 | 11/2008 | De Boni et al. |
| 2010/0175202 A1 | 7/2010 | Simonet et al. |
| 2010/0192969 A1* | 8/2010 | DeGeorge ............ A61K 8/23 132/208 |
| 2010/0199441 A1 | 8/2010 | Hercouet et al. |
| 2011/0117037 A1 | 5/2011 | Legrand et al. |
| 2011/0150797 A1 | 6/2011 | Legrand et al. |
| 2011/0203605 A1 | 8/2011 | Allard et al. |
| 2011/0203606 A1 | 8/2011 | Recchion et al. |
| 2011/0209720 A1 | 9/2011 | DeGeorge et al. |
| 2012/0076930 A1 | 3/2012 | Miller |
| 2012/0210523 A1 | 8/2012 | Lalleman et al. |
| 2013/0042883 A1 | 2/2013 | DeGeorge et al. |
| 2013/0167862 A1 | 7/2013 | Lopez et al. |
| 2014/0082855 A1 | 3/2014 | Rapold et al. |
| 2014/0305464 A1 | 10/2014 | DeGeorge et al. |
| 2014/0326270 A1 | 11/2014 | DeGeorge et al. |
| 2015/0143637 A1* | 5/2015 | Rapold .............. A61Q 5/10 8/406 |
| 2015/0335545 A1* | 11/2015 | Rapold .............. A61K 8/463 8/416 |
| 2016/0279036 A1 | 9/2016 | Schoepgens et al. |
| 2017/0172901 A1 | 6/2017 | Kerl et al. |
| 2017/0354584 A1 | 12/2017 | Lalleman et al. |

FOREIGN PATENT DOCUMENTS

| | | |
|---|---|---|
| DE | 4133957 A1 | 4/1993 |
| DE | 19543988 A1 | 5/1997 |
| EP | 0080976 A1 | 6/1983 |
| EP | 0122324 A1 | 10/1984 |
| EP | 0337354 A1 | 10/1989 |
| EP | 0770375 A1 | 5/1997 |
| FR | 1492597 A | 8/1967 |
| FR | 1583363 A | 10/1969 |
| FR | 2077143 A5 | 10/1971 |
| FR | 2080759 A1 | 11/1971 |
| FR | 2162025 A | 7/1973 |
| FR | 2190406 A2 | 2/1974 |
| FR | 2252840 A1 | 6/1975 |
| FR | 2270846 A1 | 12/1975 |
| FR | 2280361 A2 | 2/1976 |
| FR | 2316271 A1 | 1/1977 |
| FR | 2320330 A1 | 3/1977 |
| FR | 2336434 A1 | 7/1977 |
| FR | 2368508 A2 | 5/1978 |
| FR | 2383660 A1 | 10/1978 |
| FR | 2393573 A1 | 1/1979 |
| FR | 2413907 A1 | 8/1979 |
| FR | 2470596 A1 | 6/1981 |
| FR | 2505348 A1 | 11/1982 |
| FR | 2519863 A1 | 7/1983 |
| FR | 2542997 A1 | 9/1984 |
| FR | 2598611 A1 | 11/1987 |
| FR | 2618070 A1 | 1/1989 |
| FR | 2633940 A1 | 7/1991 |
| FR | 2733749 A1 | 11/1996 |
| FR | 2801308 A1 | 5/2001 |
| FR | 2886136 A1 | 12/2006 |
| FR | 3008615 A1 | 1/2015 |
| GB | 1026978 A | 4/1966 |
| GB | 1153196 A | 5/1969 |
| GB | 1546809 A | 5/1979 |
| GB | 2207443 A * | 2/1989 | ............... A61K 8/13 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 96/15765 A1 | 5/1996 |
| WO | 2016/091816 A1 | 6/2016 |
| WO | 2018/056235 A1 | 3/2018 |
| WO | 2019/243505 A1 | 12/2019 |
| WO | 2019/243507 A1 | 12/2019 |
| WO | 2019/243509 A1 | 12/2019 |
| WO | 2019/243511 A1 | 12/2019 |
| WO | 2019/243512 A1 | 12/2019 |
| WO | 2019/243513 A1 | 12/2019 |

OTHER PUBLICATIONS

International Search Report and Written Opinion for counterpart Application No. PCT/EP2019/066368, dated Sep. 3, 2019.
International Search Report and Written Opinion for counterpart Application No. PCT/EP2019/066363, dated Sep. 2, 2019.
International Search Report and Written Opinion for counterpart Application No. PCT/EP2019/066369, dated Aug. 22, 2019.
International Search Report and Written Opinion for counterpart Application No. PCT/EP2019/066364, dated Sep. 11, 2019.
International Search Report and Written Opinion for counterpart Application No. PCT/EP2019/066361, dated Aug. 22, 2019.
International Search Report and Written Opinion for counterpart Application No. PCT/EP2019/066370, dated Sep. 11, 2019.

(56) References Cited

OTHER PUBLICATIONS

Mintel, "Root Vanish," Kazumi, ID 3319563, XP055562798, dated Feb. 27, 2015.
Mintel, "Colourant Cream," LG Household and Health Care, ID 1533817, , XP055547325, dated May 11, 2011.
Mintel, "Hair Colourant," Garnier, ID 644332, XP055547333, dated Jan. 16, 2007.
Non-Final Office Action for copending U.S. Appl. No. 17/252,856, dated Aug. 16, 2021.
Non-Final Office Action for copending U.S. Appl. No. 17/252,883, dated Aug. 18, 2021.
Non-Final Office Action for copending U.S. Appl. No. 17/253,035, dated Aug. 20, 2021.
Non-Final Office Action for copending U.S. Appl. No. 17/252,870, dated Sep. 10, 2021.
Non-Final Office Action for copending U.S. Appl. No. 17/252,974, dated Sep. 20, 2021.
Non-Final Office Action for copending U.S. Appl. No. 17/253,019, dated Sep. 24, 2021.
Final Office Action for copending U.S. Appl. No. 17/252,974, dated Dec. 29, 2021.

\* cited by examiner

HAIR DYEING METHOD USING A DYE COMPOSITION AND AN OXIDIZING COMPOSITION, SAID COMPOSITIONS COMPRISING A SCLEROGLUCAN GUM

CROSS REFERENCE TO RELATED APPLICATION

This is a national stage application of PCT/EP2019/066364, filed internationally on Jun. 20, 2019, which claims priority to French Application No. 1855429, filed on Jun. 20, 2018, both of which are incorporated by reference herein in their entireties.

The present invention relates to a process for dyeing keratin fibers, in particular human keratin fibers such as the hair, involving applying to the fibers a dye composition (A) comprising one or more oxidation dyes, one or more scleroglucan gums in a total weight content of greater than or equal to 0.5% relative to the total weight of composition (A) and one or more alkaline agents, and an oxidizing composition (B) comprising one or more chemical oxidizing agents and one or more scleroglucan gums preferably in a total weight content of greater than or equal to 0.5% relative to the total weight of composition (B), the oxidizing composition (B) being mixed with the dye composition (A) just before use (application to said fibers) (extemporaneously).

The invention also relates to a multi-compartment device suitable for performing said dyeing process.

The present invention relates to the field of dyeing keratin fibers and more particularly to the field of hair dyeing.

Among the methods for dyeing human keratin fibers, such as the hair, mention may be made of oxidation dyeing or permanent dyeing. More particularly, this form of dyeing uses one or more oxidation dyes, usually one or more oxidation bases optionally combined with one or more couplers.

In general, oxidation bases are chosen from ortho- or para-phenylenediamines, ortho- or para-aminophenols and heterocyclic compounds. These oxidation bases are colorless or weakly colored compounds which, when combined with oxidizing products, can give access to colored species.

The shades obtained with these oxidation bases are quite often varied by combining them with one or more couplers, these couplers being notably chosen from aromatic meta-diamines, meta-aminophenols, meta-diphenols and certain heterocyclic compounds such as indole compounds.

The variety of molecules used as oxidation bases and couplers allows a wide range of colors to be obtained.

It is also possible to add to these compositions direct dyes, which are colored, and coloring molecules that have affinity for fibers. The direct dyes generally used are chosen from nitrobenzene, anthraquinone, nitropyridine, azo, methine, azomethine, xanthene, acridine, azine and triarylmethane direct dyes. The presence of such compounds enables the coloring obtained to be further enriched with glints or enables the chromaticity of the coloring obtained to be increased.

Oxidation dyeing processes thus consist in using with these dye compositions a composition comprising at least one oxidizing agent, generally hydrogen peroxide, under alkaline pH conditions in the vast majority of cases. The role of this oxidizing agent is to reveal the coloring, via an oxidative condensation reaction between the oxidation dyes.

Oxidation dyeing must moreover satisfy a certain number of requirements. Thus, it must be free of toxicological drawbacks, it must enable shades to be obtained in the desired intensity and it must show a good wear property in the face of external attacking factors such as light, bad weather, washing, permanent waving, perspiration and rubbing.

The dyeing process must also make it possible to cover gray hair and, finally, must be as unselective as possible, i.e. it must produce the smallest possible color differences along the same keratin fiber, which generally includes areas that are differently sensitized (i.e. damaged) from its end to its root, so as to obtain the most uniform possible coloring of the keratin fibers. Dye compositions must also give good cosmetic properties to keratin fibers, in particular care, softness and/or hold, and must have good working qualities, in particular they must be easy to apply, while at the same time achieving visible (i.e. notably intense, chromatic), uniform and fast coloring results.

The compositions used in a dyeing process must also have good mixing and application properties on keratin fibers, and notably good rheological properties so as not to run down the face, onto the scalp or beyond the areas that it is proposed to dye, when they are applied; this notably allows uniform application from the roots to the ends.

In particular, it is sought to obtain dye compositions or oxidizing compositions that are stable over time for several weeks. For the purposes of the present invention, the term "stable" in particular means that physical properties such as the appearance, the pH and/or the viscosity vary little or not at all over time, and in particular that the viscosity of the composition does not change or changes little during storage and/or that the composition does not undergo phase separation during storage.

Specifically, it is desirable for the dye compositions or oxidizing compositions to be stable over time, in particular stable after 1 month at 45° C., or even after 2 months at 45° C.

It is also sought to obtain dye compositions that are stable over a wide pH range and in particular with respect to extreme pH values, for example to alkaline pH values ranging from 9 to 12. Finally, the dye compositions may occasionally be destabilized (undergo phase separation) by high contents of certain compounds, and it is thus desirable for these compositions to be stable under these conditions, in particular for them not to undergo phase separation.

Thus, one of the objects of the present invention is to propose a process for dyeing keratin fibers, preferably human keratin fibers such as the hair, which do not have the drawbacks mentioned above, i.e. which is capable of giving very good dyeing performance qualities, notably in terms of intensity and/or color build-up, and also in terms of selectivity, chromaticity and/or resistance to external agents, having good working qualities in particular when applied to keratin fibers, and giving the fibers good cosmetic properties (softness, smoothness), the compositions used being stable (notably not undergoing phase separation and/or having a viscosity or a pH which changes little or not at all over time).

Advantageously, the dye compositions and/or oxidizing compositions used in the process according to the invention are translucent. Specifically, a translucent dye product offers the consumer the possibility of visualizing the change in the color result during the time that the product is left on, affording him or her the choice of stopping at the moment that the result suits them. Furthermore, by virtue of their very stable and similar rheological properties of the dye compositions and oxidizing compositions used and optionally allow the use of packaging as an aerosol for the implementation of the process according to the invention.

These aims and others are achieved by the present invention, one subject of which is thus a process for dyeing keratin fibers, preferably human keratin fibers such as the hair, involving the application to the fibers:
a) of a dye composition (A) comprising:
one or more oxidation dyes;
one or more scleroglucan gums in a total content of greater than or equal to 0.5% by weight relative to the total weight of the composition;
one or more alkaline agents; and
b) of an oxidizing composition (B) comprising:
one or more chemical oxidizing agents, preferably chosen from hydrogen peroxide and/or one or more systems for generating hydrogen peroxide, preferably hydrogen peroxide; and
one or more scleroglucan gums, preferably in a total weight content of greater than or equal to 0.5% relative to the total weight of composition (B);
the oxidizing composition (B) being mixed with the dye composition (A) just before use (i.e. application to said fibers) (extemporaneously).

A subject of the invention is also a multi-compartment device (or "kit") for implementing the process for dyeing keratin fibers, preferably comprising at least two compartments, a first compartment containing the dye composition (A) as defined previously, and the second compartment containing the oxidizing composition (B) as defined previously and the compositions in the compartments being intended to be mixed before application, to give the formulation after mixing; in particular, the kit may be an aerosol device.

For the purposes of the present invention, the term "composition for dyeing" or "dye composition" means a composition intended to be applied to keratin fibers, preferably human keratin fibers and in particular the hair, in particular after mixing with an oxidizing composition (B) as defined previously comprising at least one chemical oxidizing agent.

For the purposes of the present invention, the term "ready-to-use dye composition" or "ready-to-use composition" means a composition resulting from mixing a dye composition and an oxidizing composition, intended to be applied immediately to the keratin fibers. The ready-to-use dye composition is advantageously prepared just before application to said keratin fibers.

For the purposes of the present invention, the term "extemporaneous" or "extemporaneously" notably means less than 30 minutes, preferably less than 15 minutes before application to the keratin fibers, preferably less than 5 minutes. In particular, the mixture is applied immediately after having been prepared. The process according to the invention can thus give very good dyeing performance on keratin fibers, notably in terms of build-up, intensity, chromaticity and/or selectivity. The process uses compositions which have good rheological properties so as not to run down onto the face, the scalp or beyond the areas that it is proposed to dye, when they are applied.

The compositions used in the process of the invention are stable. For the purposes of the present invention, the term "stable" in particular means that physical properties such as the appearance, the pH and/or the viscosity vary little or not at all over time, and in particular that the viscosity of the composition does not change or changes little during storage and/or that the composition does not undergo phase separation during storage. In particular, it is desirable for the dye compositions to be stable over time, in particular stable after 1 month at 45° C., or even after 2 months at 45° C.

Furthermore, the compositions used in the process according to the invention have the advantage of being stable (of not undergoing phase separation) independently of the pH and in particular with respect to extreme pH values (for example alkaline pH values ranging from 9 to 12). Finally, the compositions are preferably stable (do not undergo phase separation) even in the presence of a high content of certain compounds, for instance oxidation dyes and/or cationic compounds, such as cationic polymers.

Moreover, the compositions used in the process according to the invention are advantageously translucent, which gives them a visual appearance that is esthetic and appealing to the consumer, as is the ready-to-use composition resulting from the mixing of the dye composition (A) and the oxidizing composition (B). This translucent dye product offers the possibility of visualizing the change in the color result during the time that the product is left on, affording the choice of stopping at the moment that the result is suitable.

Furthermore, by virtue of their very stable and similar rheological properties, the dye compositions and oxidizing compositions used mix particularly easily and optionally allow the use of packaging as an aerosol for the implementation of the process according to the invention. Other features and advantages of the invention will emerge more clearly on reading the description and the examples that follow.

In the text hereinbelow, unless otherwise indicated, the limits of a range of values are included in that range, notably in the expressions "between" and "ranging from . . . to . . . ".

The keratin fibers are preferably human keratin fibers, preferably the hair.

The expression "at least one" is equivalent to the expression "one or more".

Advantageously, the dye composition (A) and the oxidizing composition (B) used in the process according to the invention have a thickened texture, in cream or gel form, and, preferably, compositions (A) and (B) are translucent.

The compositions used in the process according to the invention generally have at room temperature a viscosity of greater than 50 cps, preferably between 200 and 100 000 cps, more preferentially between 400 and 50 000 cps and even more preferentially between 500 and 10 000 cps, better still between 600 and 8000 cps. This viscosity is measured at 25° C. at a shear rate of 200 rpm using a rheometer such as a Rheomat RM 180 equipped with a No. 3 or 4 spindle, the measurement being performed after 60 minutes of rotation of the spindle (after which time stabilization of the viscosity and of the spin speed of the spindle are observed).

Dye Composition (A)

Oxidation Dyes

The dye composition (A) according to the invention comprises one or more oxidation dyes.

The oxidation dye precursors that may be used in the present invention are generally chosen from oxidation bases, optionally combined with one or more couplers.

The oxidation bases may preferably be chosen from para-phenylenediamines, bis(phenyl)alkylenediamines, para-aminophenols, ortho-aminophenols and heterocyclic bases, and the addition salts thereof.

Preferentially, the oxidation base(s) of the invention are chosen from para-phenylenediamines and heterocyclic bases. Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, 2-methoxymethyl-para-phenylenediamine, N,N-dimethyl-3-methyl-para-phenylenediamine, N-ethyl-N-(β-hydroxyethyl)-para-phenylenediamine, N-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine and 2-methoxymethyl-para-phenylenediamine, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxy methyl phenol, 4-amino-2-methoxymethylphenol, 4-amino-2-aminomethylphenol, 4-amino-2-(-hydroxyethylaminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol, 5-acetamido-2-aminophenol and the addition salts thereof.

Among the heterocyclic bases, mention may be made in particular of pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or addition salts thereof described, for example, in patent application FR 2 801 308.

Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino] ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-β-hydroxyethoxy-3-aminopyrazolo[1,5-a]pyridine and 2-(4-dimethylpiperazinium-1-yl)-3-aminopyrazolo pyridine, and also the addition salts thereof.

More particularly, the oxidation bases according to the invention are chosen from 3-aminopyrazolo[1,5-a]pyridines preferably substituted in position 2 with:

a) a (di)($C_1$-$C_6$)(alkyl)amino group, the alkyl groups possibly being substituted with one or more hydroxyl, amino or imidazolium groups;

b) a cationic or non-cationic 5- to 7-membered heterocycloalkyl group comprising from 1 to 3 heteroatoms, optionally substituted with one or more ($C_1$-$C_6$)alkyl groups such as di($C_1$-$C_4$)alkylpiperazinium;

c) a ($C_1$-$C_6$)alkoxy group optionally substituted with one or more hydroxyl groups, such as β-hydroxyalkoxy, and also the addition salts thereof.

Among the pyrimidine derivatives, mention may be made of the compounds described, for example, in patents DE 2359399, JP 88169571, JP 05-63124 and EP 0/770/375 or patent application WO 96/15765, such as 2,4,5,6-tetraaminopyrimidine, 4-hydroxy-2,5,6-triaminopyrimidine, 2-hydroxy-4,5 aminopyrimidine, 2,4-dihydroxy-5,6-diaminopyrimidine, 2,5,6-triaminopyrimidine and the addition salts thereof, and the tautomeric forms thereof, when a tautomeric equilibrium exists.

Among the pyrazole derivatives, mention may be made of the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, amino-3-methyl-phenylpyrazole, 4,5-diamino-1-methyl-3-phenylpyrazole, 4-amino-1,3-dimethyl-5-hydrazinopyrazole, enzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and the addition salts thereof. Preferably, the heterocyclic oxidation bases of the invention are chosen from 4,5-diaminopyrazoles such as 4,5-diamino-1-(β-hydroxyethyl)pyrazole. Use may also be made of 4,5-diamino-1-β-methoxyethyl)pyrazole.

Use will preferably be made of a 4,5-diaminopyrazole and even more preferentially of 4,5-diamino-1-β-hydroxyethyl) pyrazole and/or a salt thereof.

Pyrazole derivatives that may also be mentioned include diamino-N,N-dihydropyrazolopyrazolones and notably those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-bis(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt thereof.

As heterocyclic bases, use will preferentially be made of 4,5-diamino-1-(β-hydroxyethyl)pyrazole and/or 2,3-diamino-6,7-dihydro-1H,5H-pyrazolo[1,2-a]pyrazol-1-one and/or a salt thereof.

The oxidation base(s) used in the context of the invention are generally present in an amount ranging from 0.001% to 10% by weight approximately, and preferably ranging from 0.005% to 5%, relative to the total weight of the dye composition.

The additional couplers that are conventionally used for the dyeing of keratin fibers are chosen from meta-phenylenediamines, meta-aminophenols, meta-diphenols, naphthalene-based couplers and heterocyclic couplers, and also the addition salts thereof.

Examples that may be mentioned include 1,3-dihydroxybenzene, 1,3-dihydroxy-2-methylbenzene, 4-chloro-1,3-dihydroxybenzene, 1-hydroxy-3-aminobenzene, 2-methyl-5-aminophenol, 3-amino-2-chloro-6-methylphenol, 2-methyl-5-hydroxyethylaminophenol, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, thymol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the invention are notably chosen from the addition salts with an acid, such as hydrochlorides, hydrobromides, sulfates, citrates, succinates, tartrates, lactates, tosylates, benzenesulfonates, phosphates and acetates.

In the context of the present invention, when they are present, the coupler(s) are generally present in a total amount ranging from 0.001% to 10% by weight approximately of the total weight of the dye composition, and preferably ranging from 0.005% to 5% by weight relative to the total weight of the dye composition (A).

Preferably, the total content of oxidation dyes in the composition according to the invention is between 0.001% and 20% by weight, preferably between 0.001% and 10% by weight, preferably between 0.01% and 5% by weight, relative to the weight of the dye composition (A).

Scleroglucan Gums

According to the invention, composition (A) comprises one or more scleroglucan gums in a total content of greater than or equal to 0.5% by weight relative to the weight of the dye composition (A).

Scleroglucan gums are polysaccharides of microbial origin produced by a fungus of Sclerotium type, in particular Sclerotium rolfsii. They are polysaccharides constituted solely of glucose units.

Scleroglucan gums may or may not be modified. Preferably, the scleroglucan gums used in the present invention are unmodified.

Examples of scleroglucan gums that may be used in the present invention are, in a nonlimiting manner, the products sold under the name Actigum CS, in particular Actigum CS 11 by the company Sanofi Bio Industries and under the name Amigum or Amigel by the company Alban Müller International.

Other scleroglucan gums, such as the gum treated with glyoxal described in French patent application No. 2 633 940, may also be used.

The scleroglucan gum(s) that may be used according to the invention preferably represent from 0.5% to 10% by weight, more preferentially from 0.5% to 5% by weight, even more preferentially from 0.5% to 3% by weight, better still from 0.5% to 2% by weight and even more preferentially from 0.7% to 1.5% by weight relative to the total weight of composition (A).

Carboxylic Acids

The dye composition (A) according to the invention may advantageously comprise one or more carboxylic acids, and/or addition salts thereof and/or solvates thereof, said carboxylic acid(s) being aliphatic compounds, comprising from 2 to 10 carbon atoms and preferably comprising at least two carboxylic groups.

Preferably, they are chosen from aliphatic dicarboxylic and or tricarboxylic acids comprising from 2 to 10 carbon atoms, preferably from 2 to 8 carbon atoms, better still from 2 to 6 carbon atoms.

In particular, the carboxylic acid(s) are saturated or unsaturated, and substituted or unsubstituted.

Preferably, the carboxylic acid(s) are chosen from the compounds having the following formula:

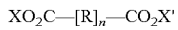

in which:

n is 0 or 1;

R is a cyclic or acyclic, preferably acyclic, saturated or unsaturated, linear or branched $C_1$-$C_8$, preferably $C_1$-$C_6$, aliphatic radical comprising between 0 and 7 unsaturations (double and/or triple bonds) and/or 0 to 2 rings, and optionally substituted with one or more substituents chosen from hydroxyl groups (—OH) and/or carboxyl groups (—COOX");

X, X' and X" independently represent a hydrogen atom, an ammonium salt, a salt of an alkali metal, such as Li, Na or K, or a salt of an alkaline-earth metal such as Be, Mg or Ca or a salt derived from an organic amine such as an alkylamine.

Preferably, in the above formula, n is 0 or 1, and R is an acyclic, saturated or unsaturated, linear or branched $C_1$-$C_6$, better still $C_1$-$C_4$ and even better still $C_1$-$C_3$, aliphatic radical comprising between 0 and 2 unsaturations (double and/or triple bonds) and optionally substituted with one or more substituents chosen from hydroxyl groups (—OH) and/or carboxyl groups (—COOX");

X, X' and X" independently represent a hydrogen atom, an ammonium salt, a salt of an alkali metal atom, such as Li, Na or K, or a salt of an alkaline-earth metal such as Be, Mg or Ca or a salt derived from an organic amine such as an alkylamine.

Even more preferentially, in the above formula, n is 0 or 1, and R is an acyclic, saturated or unsaturated, linear or branched $C_1$-$C_4$ aliphatic alkyl or alkenyl radical comprising from 0 to 1 unsaturation, optionally substituted with one or more substituents chosen from hydroxyl groups (—OH) and/or carboxyl groups (—COOX"). Preferably, n is 1.

The term "aliphatic radical" means a saturated or unsaturated nonaromatic hydrocarbon-based radical, which may be an open-chain (linear or branched) hydrocarbon or an alicyclic radical (i.e. a radical comprising one or more nonaromatic rings), and may optionally be substituted with one or more carboxyl and/or hydroxyl groups.

Since the carboxylic acid(s) are aliphatic, they therefore do not comprise an aromatic ring.

Preferably, the carboxylic acids may be chosen from oxalic acid, malonic acid, malic acid, glutamic acid, citraconic acid, citric acid, maleic acid, succinic acid, adipic acid, tartaric acid, fumaric acid, and mixtures thereof.

Preferably, the carboxylic acid(s) comprise at least two carboxylic groups and are chosen from malonic acid, citric acid, maleic acid, glutaric acid, succinic acid, and mixtures thereof; preferably chosen from malonic acid, citric acid, maleic acid, and mixtures thereof.

More particularly preferably, the carboxylic acid is citric acid.

The total content of carboxylic acid(s) and/or addition salts thereof and/or solvates thereof preferably ranges from 0.1% to 20% by weight, relative to the total weight of composition (A).

Preferably, the total content of carboxylic acid(s) ranges from 0.1% to 20%, preferentially from 0.5% to 10% by weight, better still from 1% to 7% by weight, relative to the total weight of the composition, and even better still from 2% to 5% by weight relative to the total weight of composition (A).

Alkaline Agents

Composition (A) used in the process according to the invention comprises one or more alkaline agents. The alkaline agent(s) (also known as basifying agents) may be mineral, organic and/or hybrid, in particular mineral and/or organic.

According to a first advantageous embodiment of the invention, the alkaline agent(s) are chosen from mineral alkaline agents, preferably chosen from aqueous ammonia, also known as ammonium hydroxide (or ammonia precursors such as ammonium salts, for example ammonium halides and in particular ammonium chloride), alkali metal or alkaline-earth metal silicates, phosphates, carbonates or bicarbonates, such as alkali metal or alkaline-earth metal metal silicates, sodium or potassium carbonate or bicarbonate, sodium or potassium hydroxide, or mixtures thereof.

Preferably according to this embodiment, the alkaline agents are chosen from aqueous ammonia (or ammonia precursors, for instance ammonium salts such as ammonium halides, in particular ammonium chloride) and/or alkali metal or alkaline-earth metal metal silicates.

According to a second advantageous embodiment of the invention, the alkaline agent(s) are chosen from organic alkaline agent(s), preferably chosen from organic amines with a $pK_b$ at 25° C. of less than 12, preferably of less than 10 and even more advantageously of less than 6. It should be noted that it is the $pK_b$ corresponding to the function which has the highest basicity. In addition, the organic amines do not comprise any alkyl or alkenyl fatty chains comprising more than ten carbon atoms.

The organic alkaline agent(s) are chosen, for example, from alkanolamines, oxyethylenated and/or oxypropylenated ethylenediamines, amino acids and the compounds of formula (XII) below:

in which W is a divalent $C_1$ to $C_6$ alkylene radical optionally substituted with one or more hydroxyl groups or a $C_1$ to $C_6$ alkyl radical, and/or optionally interrupted with one or more heteroatoms such as O, or $NR_u$; $R_x$, $R_y$, $R_z$, $R_t$, and $R_u$, which may be identical or different, represent a hydrogen atom, or a $C_1$ to $C_6$ alkyl or $C_1$ to $C_6$ hydroxyalkyl or $C_1$ to $C_6$ aminoalkyl radical.

Examples of amines of formula (XII) that may be mentioned include 1,3-diaminopropane, 1,3-diamino-2-propanol, spermine and spermidine.

According to a preferred embodiment, the organic alkaline agent(s) are chosen from alkanolamines and/or amino acids.

According to a first preferred embodiment, the alkaline agent(s) are chosen from alkanolamines.

The term "alkanolamine" means an organic amine comprising a primary, secondary or tertiary amine function, and one or more linear or branched $C_1$ to $C_8$ alkyl groups bearing one or more hydroxyl radicals.

Organic amines chosen from alkanolamines such as monoalkanolamines, dialkanolamines or trialkanolamines comprising one to three identical or different $C_1$ to $C_4$ hydroxyalkyl radicals are in particular suitable for performing the invention.

The compounds of this type are preferably chosen from monoethanolamine (MEA), diethanolamine, triethanolamine, monoisopropanolamine, diisopropanolamine, N,N-dimethyl ethanol amine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane, and mixtures thereof, preferably monoethanolamine (MEA).

According to a second preferred embodiment, the alkaline agent(s) are chosen from amino acids.

More particularly, the amino acids that may be used are of natural or synthetic origin, in their L, D or racemic form, and include at least one acid function chosen more particularly from carboxylic acid, sulfonic acid, phosphonic acid and phosphoric acid functions. The amino acids may be in neutral or ionic form.

As amino acids that may be used in the composition according to the present invention, mention may notably be made of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are chosen from basic amino acids, notably comprising an additional amine function optionally included in a ring or in a ureido function.

Such basic amino acids are preferably chosen from those corresponding to formula (XIII) below, and also salts thereof:

$$R\text{—}CH_2\text{—}CH(NH_2)\text{—}C(O)\text{—}OH \qquad (XIII)$$

in which R represents a group chosen from imidazolyl, preferably imidazolyl-4-yl; aminopropyl; aminoethyl; —$(CH_2)_2$N(H)—C(O)—$NH_2$; and —$(CH_2)_2$—N(H)—C(NH)—$NH_2$.

The compounds corresponding to formula (XIII) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made notably of carnosine, anserine and balenine.

The organic amine may also be chosen from compounds including a guanidine function. As amines of this type that may be used in the present invention, besides arginine, which has already been mentioned as an amino acid, mention may be made notably of creatine, creatinine, 1,1-dimethylguanidine, 1,1-diethylguanidine, glycocyamine, metformin, agmatine, n-amidinoalanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Preferably, the alkaline agent(s) present in composition (A) used in the process according to the invention are chosen from aqueous ammonia, alkanolamines and/or amino acids in neutral or ionic form, in particular basic amino acids, and preferably corresponding to those of formula (XIII), such as arginine, and alkali metal or alkaline-earth metal metasilicates.

Preferably, the composition according to the invention comprises one or more alkaline agents.

According to a particularly preferred embodiment of the invention, composition (A) used in the process according to the invention comprises:

one or more mineral alkaline agents, preferably chosen from aqueous ammonia and/or alkali metal or alkaline-earth metal metal silicates, preferably aqueous ammonia; and one or more organic agents, preferably chosen from alkanolamines and/or amino acids, preferably from alkanolamines, preferably monoethanolamine.

Composition (A) according to the invention preferably comprises one or more alkaline agents; it preferably comprises one or more mineral alkaline agents and one or more alkaline agents chosen from alkanolamine(s).

When composition (A) comprises aqueous ammonia (ammonium hydroxide), its content preferably ranges from 0.1% to 10% by weight, more preferentially from 0.5% to 8% by weight and better still from 1% to 6% by weight, relative to the total weight of composition (A).

When composition (A) comprises one or more alkanolamines, their content preferably ranges from 0.5% to 10% by weight, more preferentially from 1% to 9% by weight and better still from 2% to 8% by weight relative to the total weight of composition (A).

Preferably, the dye composition (A) used in the process according to the invention comprises a total content of alkaline agents ranging from 1% to 20% by weight, more preferentially from 3% to 18% by weight and better still from 5% to 16% by weight relative to the total weight of composition (A).

Associative Polymers

The dye composition (A) used in the process according to the invention may also comprise one or more associative polymers. The associative polymers according to the invention are polymers comprising at least one $C_8$-$C_{30}$ fatty chain and of which the molecules are capable, in the formulation medium, of associating with each other or with molecules of other compounds.

Preferably, the fatty chain includes from 10 to 30 carbon atoms.

A particular case of associative polymers is amphiphilic polymers, i.e. polymers including one or more hydrophilic parts which make them water-soluble and one or more hydrophobic zones (comprising at least one fatty chain) via which the polymers interact and assemble with each other or with other molecules.

The associative polymers that may be used in the composition according to the invention may be chosen from nonionic, anionic, cationic and amphoteric associative polymers, and mixtures thereof.

In particular, the associative polymer(s) are nonionic, and preferably chosen from celluloses modified with groups including at least one fatty chain. Preferably, the nonionic associative polymer(s) are chosen from hydroxyethylcelluloses modified with groups including at least one fatty chain, such as alkyl, aralkyl, alkylaryl groups, or mixtures thereof, and in which the alkyl groups are preferably $C_8$-$C_{22}$, and hydroxyethylcelluloses modified with polyalkylene glycol alkyl phenyl ether groups, and mixtures thereof, preferably cetylhydroxyethylcellulose.

According to a third embodiment, the associative polymer(s) are chosen from cationic associative polymers. The associative polymers of cationic type are preferably chosen from quaternized cellulose derivatives, polyacrylates bearing noncyclic amine side groups, cationic polyurethanes, cationic polyvinyllactams and the acrylic terpolymer whose constitution is given below.

Cationic Polymers

According to an advantageous embodiment of the invention, composition (A) comprises one or more cationic polymers.

As examples of cationic polymers that may be used in the compositions according to the invention, mention may be made in particular of:

(1) cyclopolymers of alkyldiallylamine or of dialkyldiallylammonium, such as the homopolymers or copolymers including, as main constituent of the chain, units corresponding to formula (I) or (II):

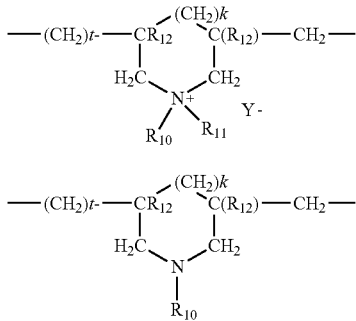

in which
  k and t are equal to 0 or 1, the sum k+t being equal to 1;
  R12 denotes a hydrogen atom or a methyl radical;
  R10 and R11, independently of each other, denote a C1-C6 alkyl group, a C1-C5 hydroxyalkyl group, a C1-C4 amidoalkyl group; or alternatively R10 and R11 may denote, together with the nitrogen atom to which they are attached, a heterocyclic group such as piperidyl or morpholinyl; R10 and R11, independently of each other, preferably denote a C1-C4 alkyl group;
  Y⁻ is an anion such as bromide, chloride, acetate, borate, citrate, tartrate, bisulfate, bisulfite, sulfate or phosphate.

Mention may be made more particularly of the dimethyldiallylammonium salt (for example chloride) homopolymer, for example sold under the name Merquat 100 by the company Nalco. Preferably, the polymers of family (1) are chosen from dialkyldiallylammonium homopolymers.

(2) quaternary diammonium polymers comprising repeating units of formula:

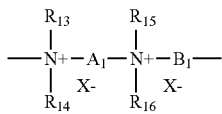

in which:
  R13, R14, R15 and R16, which may be identical or different, represent aliphatic, alicyclic or arylaliphatic radicals comprising from 1 to 20 carbon atoms or C1-C12 hydroxyalkyl aliphatic radicals,
  or else R13, R14, R15 and R16, together or separately, form, with the nitrogen atoms to which they are attached, heterocycles optionally comprising a second non-nitrogen heteroatom;
  or else R13, R14, R15 and R16 represent a linear or branched C1-C6 alkyl radical substituted with a nitrile, ester, acyl, amide or —CO—O—R17-D or —CO—NH—R17-D group, where R17 is an alkylene and D is a quaternary ammonium group;
  A1 and B1 represent linear or branched, saturated or unsaturated, divalent polymethylene groups comprising from 2 to 20 carbon atoms, which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and
  X⁻ denotes an anion derived from a mineral or organic acid;
  it being understood that A1, R13 and R15 can form, with the two nitrogen atoms to which they are attached, a piperazine ring;
  in addition, if A1 denotes a linear or branched, saturated or unsaturated alkylene or hydroxyalkylene radical, B1 may also denote a group (CH2)n-CO-D-OC—(CH2)p- with n and p, which may be identical or different, being integers ranging from 2 to 20, and D denoting:
    a) a glycol residue of formula —O—Z—O—, in which Z denotes a linear or branched hydrocarbon-based radical or a group corresponding to one of the following formulae: —(CH2CH2O)x-CH2CH2- and —[CH2CH(CH3)O]y-CH2CH(CH3)-, in which x and y denote an integer from 1 to 4, representing a defined and unique degree of polymerization or any number from 1 to 4 representing an average degree of polymerization;
    b) a bis-secondary diamine residue, such as a piperazine derivative;
    c) a bis-primary diamine residue of formula —NH—Y—NH—, in which Y denotes a linear or branched hydrocarbon-based radical, or else the divalent radical —CH2-CH2-S—S—CH2-CH2-;
    d) a ureylene group of formula —NH—CO—NH—.

Preferably, X⁻ is an anion, such as chloride or bromide. These polymers have a number-average molar mass (Mn) generally of between 1000 and 100 000.

Mention may be made more particularly of cationic polymers that are constituted of repeating units corresponding to the formula:

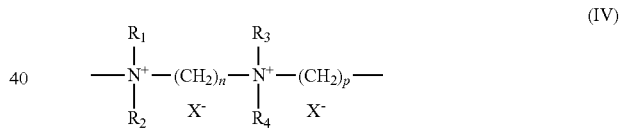

in which R1, R2, R3 and R4, which may be identical or different, denote an alkyl or hydroxyalkyl radical containing from 1 to 4 carbon atoms, n and p are integers ranging from 2 to 20, and X— is an anion derived from a mineral or organic acid.

A particularly preferred compound of formula (IV) is the one for which R1, R2, R3 and R4 represent a methyl radical and n=3, p=6 and X=Cl, known as Hexadimethrine chloride according to the INCI (CTFA) nomenclature.

Preferably, the cationic polymer(s) are chosen from dialkyldiallylammonium homopolymers, in particular homopolymers of dimethyldiallylammonium salts, polymers constituted of repeating units corresponding to formula (IV) above, in particular poly(dimethyliminio)-1,3-propanediyl (dimethyliminio)-1,6-hexanediyl dichloride, the INCI name of which is hexadimethrine chloride, and mixtures thereof.

When they are present, the total content of cationic polymers (other than the associative polymers and the fixing polymers) in composition (A) may range from 0.01% to 10% by weight relative to the weight of the composition, preferably from 0.1% to 7% relative to the weight of the composition, even more advantageously from 0.5% to 5% by weight and better still from 0.5% to 3% by weight relative to the weight of composition (A).

Surfactants

Preferably, composition (A) comprises one or more surfactants, which may be chosen from anionic surfactants, amphoteric or zwitterionic surfactants, nonionic surfactants and cationic surfactants, and mixtures thereof, preferably from nonionic surfactants, cationic surfactants, and mixtures thereof.

The term "anionic surfactant" means a surfactant including, as ionic or ionizable groups, only anionic groups. These anionic groups are preferably chosen from the following groups: $CO_2H$, $CO_2^-$, $SO_3H$, $SO_3^-$, $OSO_3H$, $OSO_3^-$, $H_2PO_3$, $HPO_3^-$, $PO_3^{2-}$, $H_2PO_2$, $HPO_2^-$, $PO_2^{2-}$ POH and $PO^-$.

The preferred surfactants are nonionic surfactants. Mention may also be made of nonionic surfactants of alkyl(poly)glycoside type, represented notably by the following general formula:

$$R_1O\text{—}(R_2O)_t\text{-}(G)_v$$

in which:
- $R_1$ represents a linear or branched alkyl or alkenyl radical including 6 to 24 carbon atoms and notably 8 to 18 carbon atoms, or an alkylphenyl radical of which the linear or branched alkyl radical includes 6 to 24 carbon atoms and notably 8 to 18 carbon atoms,
- $R_2$ represents an alkylene radical including 2 to 4 carbon atoms,
- G represents a sugar unit including 5 to 6 carbon atoms,
- t denotes a value ranging from 0 to 10 and preferably from 0 to 4,
- v denotes a value ranging from 1 to 15 and preferably from 1 to 4.

Preferably, the alkyl(poly)glycoside surfactants are compounds of the formula described above in which:
- $R_1$ denotes a linear or branched, saturated or unsaturated alkyl radical including from 8 to 18 carbon atoms,
- $R_2$ represents an alkylene radical including 2 to 4 carbon atoms,
- t denotes a value ranging from 0 to 3 and preferably equal to 0,
- G denotes glucose, fructose or galactose, preferably glucose;
- the degree of polymerization, i.e. the value of v, possibly ranging from 1 to 15 and preferably from 1 to 4; the mean degree of polymerization more particularly being between 1 and 2.

The glucoside bonds between the sugar units are generally of 1-6 or 1-4 type and preferably of 1-4 type. Preferably, the alkyl(poly)glycoside surfactant is an alkyl(poly)glucoside surfactant. $C_8/C_{16}$-Alkyl(poly)glucosides 1,4, and notably decyl glucosides and caprylyl/capryl glucosides, are most particularly preferred, preferably caprylyl/capryl glucosides.

Among the commercial products, mention may be made of the products sold by the company Cognis under the names Plantaren® (600 CS/U, 1200 and 2000) or Plantacare® (818, 1200 and 2000); the products sold by the company SEPPIC under the names Oramix CG 110 and Oramix® NS 10; the products sold by the company BASF under the name Lutensol GD 70, or the products sold by the company Chem Y under the name AG10 LK.

Preferably, use is made of $C_8/C_{16}$-alkyl (poly)glycosides 1,4, notably as an aqueous 53% solution, such as those sold by Cognis under the reference Plantacare® 818 UP.

Preferentially, the nonionic surfactants are chosen from:
- saturated or unsaturated, linear or branched, oxyethylenated fatty alcohols including at least one $C_8$ to $C_{40}$, notably $C_8$-$C_{20}$ and better still $C_{10}$-$C_{18}$ alkyl chain, and comprising from 1 to 100 mol of ethylene oxide, preferably from 2 to 50, more particularly from 2 to 40 mol, or even from 3 to 20 mol of ethylene oxide; and
- ($C_6$-$C_{24}$ alkyl)(poly)glycosides, and more particularly ($C_8$-$C_{18}$ alkyl)(poly)glycosides;

and mixtures thereof;

and even more preferentially from ($C_6$-$C_{24}$ alkyl)(poly)glycosides, preferentially ($C_8$-$C_{18}$ alkyl)(poly)glycosides.

According to a preferred embodiment of the invention, composition (A) comprises one or more nonionic surfactants preferably chosen from alkyl(poly)glycosides. Preferably, the composition according to the invention comprises one or more surfactants chosen from ($C_6$-$C_{24}$ alkyl)(poly)glycosides, more preferentially from ($C_8$-$C_{18}$ alkyl)(poly)glycosides, preferably from $C_8/C_{16}$-(poly)glucosides, preferably of 1,4 type, and preferably chosen from decyl glucosides and/or caprylyl/caprylyl glucosides and/or cocoyl glucosides.

According to a first embodiment, the surfactant(s) are nonionic, preferably chosen from ($C_6$-$C_{24}$ alkyl)polyglycosides.

According to a preferred embodiment, composition (A) comprises at least one or more cationic surfactants. Preferably, the cationic surfactant(s) are chosen from optionally polyoxyalkylenated primary, secondary or tertiary fatty amine salts, quaternary ammonium salts, and mixtures thereof.

Examples of quaternary ammonium salts that may notably be mentioned include:

those corresponding to the general formula (X) below:

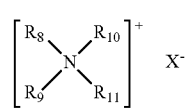

(X)

in which the groups $R_8$ to $R_{11}$, which may be identical or different, represent a linear or branched aliphatic group including from 1 to 30 carbon atoms, or an aromatic group such as aryl or alkylaryl, at least one of the groups $R_8$ to $R_{11}$ including from 8 to 30 carbon atoms and preferably from 12 to 24 carbon atoms. The aliphatic groups may include heteroatoms notably such as oxygen, nitrogen, sulfur and halogens.

The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate, $C_1$-$C_{30}$ hydroxyalkyl groups, $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts of formula (X), preference is given, firstly, to tetraalkylammonium chlorides, for instance dialkyldimethylammonium or alkyltrimethylammonium chlorides in which the alkyl group includes from about 12 to 22 carbon atoms, in particular behenyltrimethylammonium chloride, distearyldimethylammonium chloride, cetyltrimethylammonium chloride or benzyldimethylstearylammonium chloride, or, secondly, to distearoylethylhydroxyethylmethylammonium methosulfate, dipalmitoylethylhydroxyethylammonium methosulfate or distearoylethylhydroxyethylammonium methosulfate, or also, finally, to palmitylamidopropyltrimethylammonium chloride or stearamidopropyldimethyl(myristyl acetate)ammonium chloride, sold under the name Ceraphyl® 70 by Van Dyk;

quaternary ammonium salts of imidazoline, for instance those of formula (XI) below:

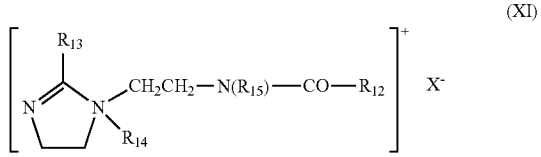

(XI)

in which $R_{12}$ represents an alkenyl or alkyl group including from 8 to 30 carbon atoms, for example derived from tallow fatty acids, $R_{13}$ represents a hydrogen atom, a $C_1$-$C_4$ alkyl group or an alkenyl or alkyl group including from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, $(C_1$-$C_4)$alkyl sulfates and $(C_1$-$C_4)$alkyl- or $(C_1$-$C_4)$alkylarylsulfonates.

Preferably, $R_{12}$ and $R_{13}$ denote a mixture of alkenyl or alkyl groups including from 12 to 21 carbon atoms, for example derived from tallow fatty acids, $R_{14}$ denotes a methyl group and $R_{15}$ denotes a hydrogen atom. Such a product is sold, for example, under the name Rewoquat® W 75 by the company Rewo, quaternary diammonium or triammonium salts, in particular of formula (XII) below:

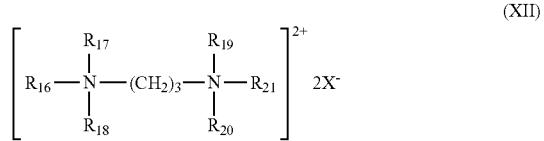

(XII)

in which $R_{16}$ denotes an alkyl group including from 16 to 30 carbon atoms, which is optionally hydroxylated and/or interrupted with one or more oxygen atoms, $R_{17}$ is chosen from hydrogen, an alkyl group including from 1 to 4 carbon atoms or a group —$(CH_2)_3$—$N^+(R_{16a})(R_{17a})(R_{18a})$, $R_{16a}$, $R_{17a}$, $R_{18a}$, $R_{18}$, $R_{19}$, $R_{20}$ and $R_{21}$, which may be identical or different, are chosen from hydrogen or an alkyl group including from 1 to 4 carbon atoms, and $X^-$ is an anion chosen from the group of halides, acetates, phosphates, nitrates, $(C_1$-$C_4)$alkyl sulfates, $(C_1$-$C_4)$alkylsulfonates or $(C_1$-$C_4)$alkylarylsulfonates, in particular methyl sulfate and ethyl sulfate.

Such compounds are, for example, Finquat CT-P, sold by the company Finetex (Quaternium 89), and Finquat CT, sold by the company Finetex (Quaternium 75);

quaternary ammonium salts containing one or more ester functions, for instance those of formula (XIII) below:

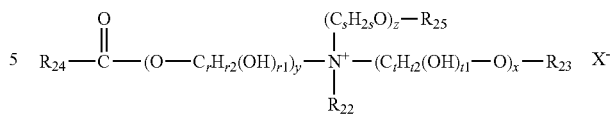

(XIII)

in which:

$R_{22}$ is chosen from $C_1$-$C_6$ alkyl groups and $C_1$-$C_6$ hydroxyalkyl or dihydroxyalkyl groups, $R_{23}$ is chosen from:

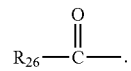

the group
linear or branched, saturated or unsaturated $C_1$-$C_{22}$ hydrocarbon-based groups $R_{27}$,
a hydrogen atom, $R_{25}$ is chosen from:

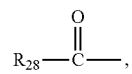

the group
linear or branched, saturated or unsaturated $C_1$-$C_6$ hydrocarbon-based groups $R_{29}$,
a hydrogen atom, $R_{24}$, $R_{26}$ and $R_{28}$, which may be identical or different, are chosen from linear or branched, saturated or unsaturated $C_7$-$C_{21}$ hydrocarbon-based groups, r, s and t, which may be identical or different, are integers ranging from 2 to 6, r1 and $t_1$, which may be identical or different, are equal to 0 or 1, r2+r1=2r and t1+t2=2t, y is an integer ranging from 1 to 10, x and z, which may be identical or different, are integers ranging from 0 to 10, $X^-$ is a simple or complex organic or inorganic anion, with the proviso that the sum x+y+z is from 1 to 15, that when x is 0 then $R_{23}$ denotes $R_{27}$, and that when z is 0 then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may be long and contain from 12 to 22 carbon atoms, or short and contain from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide, preferably chloride, bromide or iodide, a ($C_1$-$C_4$)alkyl sulfate or a ($C_1$-$C_4$)alkyl- or ($C_1$-$C_4$)alkylarylsulfonate. However, use may be made of methanesulfonate, phosphate, nitrate, tosylate, an anion derived from an organic acid, such as acetate or lactate, or any other anion that is compatible with the ammonium bearing an ester functional group.

The anion $X^-$ is even more particularly chloride, methyl sulfate or ethyl sulfate.

Use is made more particularly, in the composition according to the invention, of the ammonium salts of formula (XIII) in which:
$R_{22}$ denotes a methyl or ethyl group,
x and y are equal to 1,
z is equal to 0 or 1,
r, s and t are equal to 2,
$R_{23}$ is chosen from:

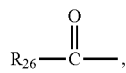

the group
methyl, ethyl or $C_{14}$-$C_{22}$ hydrocarbon-based groups,
a hydrogen atom,
$R_{25}$ is chosen from:

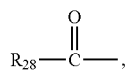

the group
a hydrogen atom,
$R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based groups are linear.

Among the compounds of formula (XIII), examples that may be mentioned include salts, notably the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are derived more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company CECA or Rewoquat® WE 18 by the company Rewo-Witco.

The composition according to the invention may contain, for example, a mixture of quaternary ammonium monoester, diester and triester salts with a weight majority of diester salts.

Use may also be made of the ammonium salts containing at least one ester function that are described in U.S. Pat. Nos. 4,874,554 and 4,137,180.

Use may also be made of the behenoylhydroxypropyltrimethylammonium chloride sold, for example, by the company Kao under the name Quartamin BTC 131.

Preferably, the ammonium salts containing at least one ester function contain two ester functions.

Preferably, the cationic surfactant(s) are chosen from cetyltrimethylammonium, behenyltrimethylammonium and dipalmitoyl-ethylhydroxyethylmethylammonium salts, and mixtures thereof, and more particularly behenyltrimethylammonium chloride, cetyltrimethylammonium chloride, and dipalmitoylethylhydroxyethylammonium methosulfate, and mixtures thereof.

Composition (A) preferably comprises one or more surfactants in a total content ranging from 0.01% to 20% by weight, more preferentially from 0.05% to 10% by weight and better still from 0.1% to 5% by weight relative to the total weight of composition (A).

Composition (A) preferably comprises one or more nonionic surfactants in a total content ranging from 0.01% to 10% by weight, more preferentially from 0.05% to 5% by weight and better still from 0.1% to 3% by weight relative to the total weight of composition (A).

Composition (A) preferably comprises one or more cationic polymers in a total content ranging from 0.01% to 10% by weight, more preferentially from 0.05% to 5% by weight and better still from 0.1% to 3% by weight relative to the total weight of composition (A).

Preferably, the surfactant(s) are chosen from cationic or nonionic surfactants, and mixtures thereof, preferentially cationic surfactants. Preferably, composition (A) comprises at least one or more cationic surfactants and one or more nonionic surfactants.

Oxidizing Composition (B)

Oxidizing Agent:

The oxidizing composition (B) used in the process according to the invention contains one or more chemical oxidizing agents, preferably chosen from hydrogen peroxide and/or one or more systems for generating hydrogen peroxide.

The term "chemical oxidizing agent" means an oxidizing agent other than atmospheric oxygen.

Preferably, the chemical oxidizing agent(s) are chosen from hydrogen peroxide, peroxygenated salts, for instance persulfates, perborates, peracids and precursors thereof, percarbonates of alkali metals or alkaline-earth metals, such as sodium carbonate peroxide, also known as sodium percarbonate and peracids and precursors thereof; alkali metal bromates or ferricyanides, solid hydrogen peroxide-generating chemical oxidizing agents such as urea peroxide and polymer complexes that can release hydrogen peroxide, notably those comprising a heterocyclic vinyl monomer such as polyvinylpyrrolidone/$H_2O_2$ complexes, in particular in powder form; oxidases that produce hydrogen peroxide in the presence of a suitable substrate (for example glucose in the case of glucose oxidase or uric acid with uricase).

Preferably, the chemical oxidizing agent(s) are chosen from hydrogen peroxide, urea peroxide, alkali metal bromates or ferricyanides, peroxygenated salts, and mixtures of these compounds.

Particularly preferably, the chemical oxidizing agent is hydrogen peroxide.

Preferably, the chemical oxidizing agent(s) represent from 0.05% to 40% by weight, preferably from 0.5% to 30% by weight, more preferentially from 1% to 20% by weight and better still from 1.5% to 15% by weight relative to the total weight of the oxidizing composition (B).

Preferably, the oxidizing composition (B) according to the invention does not contain any peroxygenated salts.

Scleroglucan Gum

As indicated previously, the oxidizing composition (B) comprises one or more scleroglucan gums, preferably in a total content of greater than or equal to 0.5% by weight relative to the weight of the composition.

Preferably, the scleroglucan gum(s) that may be used according to the invention preferably represent from 0.5% to 10% by weight, more preferentially from 0.5% to 5% by weight, even more preferentially from 0.5% to 3% by weight or even from 0.7% to 2% by weight relative to the total weight of the oxidizing composition (B).

Phosphorus-Based Sequestrants

Preferably, according to the invention, composition (B) comprises one or more phosphorus-based sequestrants.

The definition of a "sequestrant" (or "chelating agent") is well known to those skilled in the art and refers to a compound or a mixture of compounds capable of forming a chelate with a metal ion. A chelate is an inorganic complex in which a compound (the sequestrant or chelating agent) is coordinated to a metal ion, i.e. it forms one or more bonds with the metal ion (formation of a ring including the metal ion).

A sequestrant (or chelating agent) generally comprises at least two electron-donating atoms which enable the formation of bonds with the metal ion.

In the context of the present invention, the sequestrant(s) are phosphorus-based sequestrants, i.e. sequestrants which comprise one or more phosphorus atoms, preferably at least two phosphorus atoms.

The phosphorus-based sequestrants used in the composition according to the invention are preferably chosen from:
inorganic phosphorus-based derivatives preferably chosen from alkali metal or alkaline-earth metal, preferably alkali metal, phosphates and pyrophosphates, such as sodium pyrophosphate, potassium pyrophosphate, sodium pyrophosphate decahydrate; and alkali metal or alkaline-earth metal, preferably alkali metal, polyphosphates, such as sodium hexametaphosphate, sodium polyphosphate, sodium tripolyphosphate, sodium trimetaphosphate; which are optionally hydrated, and mixtures thereof;
organic phosphorus-based derivatives, such as organic (poly)phosphates and (poly)phosphonates, such as etidronic acid and/or alkali metal or alkaline-earth metal salts thereof, for instance tetrasodium etidronate, and mixtures thereof.

Preferably, the phosphorus-based sequestrant(s) are chosen from linear or cyclic compounds comprising at least two phosphorus atoms bonded together covalently via at least one linker L comprising at least one oxygen atom and/or at least one carbon atom.

In one embodiment, the phosphorus-based sequestrant(s) are chosen from inorganic phosphorus-based derivatives, preferably comprising at least two phosphorus atoms. More preferentially, the phosphorus-based sequestrant(s) are chosen from alkali metal or alkaline-earth metal pyrophosphates, better still from alkali metal pyrophosphates, in particular sodium pyrophosphate (also known as tetrasodium pyrophosphate).

In another embodiment, the phosphorus-based sequestrant(s) are chosen from organic phosphorus-based derivatives, preferably comprising at least two phosphorus atoms. More preferentially, the phosphorus-based sequestrant(s) are chosen from etidronic acid (also known as 1-hydroxyethane-1,1-diphosphonic acid) and/or alkali metal or alkaline-earth metal, preferably alkali metal, salts thereof, for instance tetrasodium etidronate.

Thus, preferably, the phosphorus-based sequestrant(s) are chosen from alkali metal pyrophosphates, etidronic acid and/or alkali metal salts thereof, and a mixture of these compounds.

Particularly preferably, the phosphorus-based sequestrant(s) are chosen from tetrasodium etidronate, etidronic acid, tetrasodium pyrophosphate, and a mixture of these compounds.

The phosphorus-based sequestrant(s) that may be used according to the invention generally represent at least 0.001% by weight, preferably from 0.001% to 5% by weight, more preferentially from 0.01% to 1% by weight and even more preferentially from 0.01% to 0.5% by weight, relative to the total weight of composition (B).

The oxidizing composition (B) may also contain various additional compounds or various adjuvants conventionally used in hair dye compositions, notably as defined previously, in particular such as one or more surfactants as described previously.

This oxidizing composition (B) may also comprise one or more water-soluble organic solvents as described below.

Finally, the oxidizing composition (B) is in various forms, for instance a solution, an emulsion or a gel.

Medium

The compositions used according to the invention are cosmetically acceptable and consequently comprise a cosmetically acceptable medium.

The term "cosmetically acceptable medium" means a medium that is compatible with keratin fibers.

The cosmetically acceptable medium that is suitable for dyeing keratin fibers, also known as a dye support, generally comprises water or a mixture of water and of at least one organic solvent to dissolve the compounds that are not sufficiently water-soluble.

More particularly, the organic solvents are chosen from linear or branched and preferably saturated monoalcohols or diols, comprising 2 to 10 carbon atoms, such as ethyl alcohol, isopropyl alcohol, hexylene glycol (2-methyl-2,4-pentanediol), neopentyl glycol and 3-methyl-1,5-pentanediol; glycerol; aromatic alcohols such as benzyl alcohol and phenylethyl alcohol; glycols or glycol ethers, for instance ethylene glycol monomethyl, monoethyl and monobutyl ethers, propylene glycol or ethers thereof, for instance propylene glycol monomethyl ether, butylene glycol or dipropylene glycol; and also diethylene glycol alkyl ethers, notably of $C_1$-$C_4$, for instance diethylene glycol monoethyl ether or monobutyl ether, alone or as a mixture.

The common solvents described above, if they are present, usually represent from 1% to 40% by weight and more preferentially from 5% to 30% by weight relative to the total weight of the composition.

The compositions used according to the invention generally comprise water or a mixture of water and of one or more organic solvents or a mixture of organic solvents.

The dye composition (A) and the oxidizing composition (B) according to the invention preferably comprise water.

Preferably, the water content ranges from 5% to 95% by weight, more preferentially from 10% to 90% by weight and better still from 20% to 80% by weight relative to the total weight of composition (A).

The oxidizing composition (B) is generally an aqueous composition. For the purposes of the invention, the term "aqueous composition" means a composition comprising more than 20% by weight of water, preferably more than 30% by weight of water and even more advantageously more than 40% by weight of water.

The oxidizing composition (B) is generally an aqueous composition. The oxidizing composition (B) usually comprises water, which generally represents from 10% to 98% by weight, preferably from 20% to 96% by weight, preferably from 50% to 95% by weight, relative to the total weight of the composition.

pH of the Medium

The pH of composition (A) used in the process according to the invention generally ranges from 1 to 12. Preferably, the pH of composition (A) according to the invention is basic.

For the purposes of the present invention, the term "basic pH" means a pH above 7.

Preferably, the pH of composition (A) according to the invention is above 8, and particularly ranges from 8.5 to 12. Preferably, the pH of the composition is between 9 and 12.

Usually, the pH of composition (B) is less than 7. The pH of composition (B) of the invention is advantageously between 1 and 7, preferably between 1 and 4 and more preferentially from 1.5 to 3.5.

pH Adjuster

The cosmetically acceptable medium may be adjusted to the desired value by means of acidifying or basifying agents usually used in the dyeing of keratin fibers, or alternatively using standard buffer systems.

Among the acidifying agents, examples that may be mentioned include mineral acids, for instance hydrochloric acid, (ortho)phosphoric acid, boric acid, nitric acid or sulfuric acid, or organic acids, for instance compounds comprising at least one sulfonic acid function, a phosphonic acid function or a phosphoric acid function, or compounds bearing a carboxylic acid function such as those mentioned previously.

Other Additives

The compositions used in the process according to the invention may also contain various additives conventionally used in hair dye compositions, such as mineral thickeners, and in particular fillers such as clays or talc; organic thickeners other than scleroglucan gums; antioxidants; penetrants; sequestrants; fragrances; dispersants; film-forming agents; ceramides; preserving agents; opacifiers; fatty substances and/or additional direct dyes.

The above additives are generally present in an amount for each of them of between 0.01% and 40% by weight relative to the weight of the composition, and preferably between 0.1% and 20% by weight relative to the weight of composition (A) and/or of composition (B).

Needless to say, a person skilled in the art will take care to select this or these additional compound(s) such that the advantageous properties intrinsically associated with the composition(s) that are useful in the dyeing process in accordance with the invention are not, or are not substantially, adversely affected by the envisioned addition(s).

Dyeing Process

According to a preferred variant of the process of the invention, a ready-to-use composition obtained by extemporaneous mixing, at the time of use, of the dye composition (A) and of the oxidizing composition (B) as defined previously is applied to wet or dry keratin materials, the weight ratio R of the amounts of (A)/(B) ranging from 0.1 to 10, preferably from 0.2 to 2 and better still from 0.3 to 1.

In addition, the application of the ready-to-use composition to the keratin materials (resulting from the extemporaneous mixing of the dye composition (A) and the oxidizing composition (B)) is left in place for a time generally from about 1 minute to 1 hour and preferably from 5 minutes to 30 minutes.

The temperature during the process is conventionally between room temperature (between 15 and 25° C.) and 80° C. and preferably between room temperature and 60° C.

After the treatment, the keratin materials are optionally rinsed with water, optionally subjected to washing followed by rinsing with water, and are then dried or left to dry.

Preferably, the keratin fibers are human keratin fibers, preferably human hair.

According to a particular embodiment of the invention, the chemical oxidizing agent(s) preferably represent a total content ranging from 0.1% to 20% by weight, preferably from 0.5% to 15% by weight or even more preferentially from 1% to 10% by weight relative to the total weight of the ready-to-use composition.

Finally, the invention relates to a multi-compartment device comprising, in a first compartment, a dye composition (A) as described previously, and, in a second, an oxidizing composition (B) as described previously.

In particular, a subject of the invention is also a multi-compartment device (or "kit") for implementing the process for dyeing keratin fibers, preferably comprising at least two compartments, a first compartment containing the dye composition (A) as defined previously, and the second compartment containing the oxidizing composition (B) as defined previously and the compositions in the compartments being intended to be mixed just before use (extemporaneously) (i.e. just before application), to give the ready-to-use formulation after mixing; in particular, the kit may be an aerosol device.

The examples that follow serve to illustrate the invention without, however, being limiting in nature.

In particular, the dyeing of the keratin fibers obtained in these examples may advantageously be evaluated in the CIE L*a*b* system, using a Datacolor Spectraflash SF600X spectrocolorimeter.

In this L*a*b* system, the three parameters respectively denote the intensity of the color (L*), the green/red color axis (a*) and the blue/yellow color axis (b*). The higher the value of L*, the lighter the color. The higher the value of a*, the redder the color and the higher the value of b*, the yellower the color.

The variation or extent of the dyeing between untreated locks of hair and locks of hair after treatment is defined by the parameter DE* and is calculated according to the following equation:

$$DE^* = \sqrt{(L^* - L_0^*)^2 + (a^* - a_0^*)^2 + (b^* - b_0^*)^2} \quad \text{(i)}$$

In this equation, the parameters L*, a* and b* represent the values measured on locks of hair after dyeing and the parameters $L_0^*$, $a_0^*$ and $b_0^*$ represent the values measured on locks of untreated hair. The higher the DE* value, the better the dyeing of the keratin fibers.

In the CIE L*, a*, b* system, the chromaticity is calculated according to the following equation:

$$C^* = \sqrt{a^{*2} + b^{*2}}$$

The higher the value of C*, the more chromatic the coloring.

EXAMPLE 1

Dye Composition

The following dye compositions were prepared from the following ingredients in the following proportions indicated in grams of active material:

|  | Comparative composition C1 outside the invention | Comparative composition C2 outside the invention | Comparative composition C3 outside the invention | Composition A1 (according to the invention) |
|---|---|---|---|---|
| Ammonium hydroxide | 2.47 | 2.47 | 2.47 | 2.47 |
| Ethanolamine | 4 | 4 | 4 | 4 |
| EDTA | 0.2 | 0.2 | 0.2 | 0.2 |
| Sodium sulfite | 0.5 | 0.5 | 0.5 | 0.5 |
| Oxidation dyes | 1.401 | 1.401 | 1.401 | 1.401 |
| Fragance | qs | qs | qs | qs |
| Hexadimethrine chloride | 0.3 | 0.3 | 0.3 | 0.3 |
| Polyquaternium-6 | 0.4 | 0.4 | 0.4 | 0.4 |
| Cetylhydroxyethyl cellulose | 0.2 | 0.2 | 0.2 | 0.2 |
| Xanthan gum | 1 | — | — | — |
| Algin | — | — | 1 | — |
| Sclerotium gum | — | — | — | 1 |
| Hydroxypropyl-cellulose | — | 1 | — | — |
| Water | qs 100 | qs 100 | qs 100 | qs 100 |
| Glycerol | 10 | 10 | 10 | 10 |
| Cetrimonium chloride | 0.25 | 0.25 | 0.25 | 0.25 |
| Caprylyl/capryl glucoside | 0.6 | 0.6 | 0.6 | 0.6 |
| Ascorbic acid | 0.4 | 0.4 | 0.4 | 0.4 |

Visual Evaluation of the Stability of the Compositions

The stability of the dye compositions was evaluated by observing the compositions at T0 (immediately after preparation of the composition) and then after 2 months of storage at 45° C.

|  | Composition C1 | Composition C2 | Composition C3 | Composition A1 |
|---|---|---|---|---|
| Observation at T0 at room temperature (25° C.) | Liquid texture Non-homogeneous (phase separation) | Liquid texture Non-homogeneous (phase separation) | Liquid texture Non-homogeneous (phase separation) | Translucent gel Homogeneous (no phase separation) |
| Observation after 2 months at 45° C. | Liquid texture Non-homogeneous (phase separation) | Liquid texture Non-homogeneous (phase separation) | Liquid texture Non-homogeneous (phase separation) | Translucent gel Homogeneous (no phase separation) |

It is observed that composition A1 according to the invention is homogeneous and forms a translucent gel at T0. After 2 months at 45°, composition A1 according to the invention is stable; it is homogeneous and translucent. Comparative compositions C1, C2 and C3 in which the scleroglucan gum was replaced weight-for-weight with another thickener of polysaccharide type are unstable. Specifically, they are not homogeneous; phase separation of these compositions is observed as early as T0.

EXAMPLE 2

Oxidizing Compositions

Preparation of the Compositions

Compositions C and B are prepared with the ingredients and the contents as indicated below.

Composition C is comparative and comprises xanthan gum. Composition B is according to the invention and comprises scleroglucan gum.

The contents are indicated as grams of starting material, unless otherwise mentioned.

| Ingredients | Composition C (comparative) | Composition B1 (invention) |
|---|---|---|
| Xanthan gum | 1.5 | — |
| Scleroglucan gum | — | 1.5 |

-continued

| Ingredients | Composition C (comparative) | Composition B1 (invention) |
|---|---|---|
| Tetrasodium etidronate | 0.06 | 0.06 |
| Tetrasodium pyrophosphate | 0.04 | 0.04 |
| Sodium salicylate | 0.035 | 0.035 |
| Hydrogen peroxide | 4.5 | 4.5 |
| Phosphoric acid | qs pH 2.2 ± 0.2 | qs pH 2.2 ± 0.2 |
| Water | qsp 100 | qsp 100 |

The T0 for the characterizations of the compositions corresponds to the state of the system 24 hours after adjusting the pH.

Characterizations of the Compositions

The viscosity of compositions B1 and C was measured during storage at atmospheric pressure, at 25° C. and at 45° C., at T0 (after adjusting the pH), at one day (T1), one week (T2) and two weeks (T3).

It is observed that composition B1 according to the invention has a low variation in viscosity over time, unlike the comparative composition C, the viscosity of which varies (decreases) more substantially over time; composition C is increasingly fluid, both at room temperature and at 45° C.

Composition B1 according to the invention thus has greater stability than comparative composition C which comprises xanthan gum. Composition B1 forms a homogeneous, translucent gel (no phase separation) after two months at room temperature and at 45° C.

EXAMPLE 3

Preparation of the Oxidizing Compositions

Composition B2 was prepared with the ingredients and the contents as indicated in the table below.

The contents are indicated as grams of starting material, unless otherwise mentioned.

| Ingredients | Composition B2 according to the invention |
|---|---|
| Scleroglucan gum | 1.5 |
| Hydrogen peroxide | 12 |
| Tetrasodium etidronate | 0.06 |
| Phosphoric acid | qs pH2.0±0.2 |
| Deionized water | qs 100 |

Composition B2 forms a homogeneous, translucent gel. It remains stable after 2 months at 25° C. and after 2 months at 45° C. No formation of bubbles is observed.

Furthermore, the viscosity of composition B2 was measured during storage at 45° C., at T0 (after adjusting the pH), at one day (T1), one week (T2) and two weeks (T3).

It is observed that composition B2 according to the invention shows a low variation in viscosity over time.

EXAMPLE 4

The following dye composition was prepared from the following ingredients in the proportions indicated in grams:

| | Composition A2 according to the invention Fiche formule |
|---|---|
| Ethanolamine | 3.23 |
| EDTA | 0.2 |
| Sodium sulfite | 0.5 |
| Toluene –2,5-diamine | 1.03 |
| 2,4-Diaminophenoxy ethanol HCl | 0.021 |
| 2-Methylresorcinol | 0.27 |
| N,N-Bis(2-hydroxyethyl)-p-phenylenediamine sulfate | 0.13 |
| Resorcinol | 0.28 |
| m-Aminophenol | 0.45 |
| Fragrance | qs |
| Cetylhydroxyethylcellulose | 0.2 |
| Sclerotium gum | 1 |
| Water | qs 100 |
| Glycerol | 10 |
| Cocoyl betaine | 0.15 |
| Caprylyl/capryl glucoside | 0.6 |
| Ascorbic acid | 0.4 |

Visual Evaluation of the Stability of the Compositions

The stability of the dye compositions was evaluated by observing the compositions at T0 (immediately after preparation of the composition) and then after 2 months of storage at room temperature (25° C.), and after 2 months of storage at 45° C.

| | Composition A2 according to the invention |
|---|---|
| Observation at T0 (immediately after preparation) | Homogeneous (no phase separation) Texture: Smooth gel |
| Observation after 2 months at 25° C. | Homogeneous (no phase separation) Texture: Smooth gel |
| Observation after 2 months at 45° C. | Homogeneous (no phase separation) Texture: Smooth gel |

It is observed that composition A2 of the process according to the invention is homogeneous and forms a translucent gel at T0, and after 2 months at room temperature or at 45° C.

The oxidizing composition B3 below was prepared from the following ingredients in the following proportions indicated in grams.

| | Fiche formule Oxidizing composition B3 according to the invention |
|---|---|
| Hydrogen peroxide | 6 |
| Phosphoric acid | qs pH = 2.2 ± 0.2 |
| Tetrasodium etidronate | 0.2 |
| Tetrasodium pyrophosphate | 0.04 |
| Sodium salicylate | 0.035 |
| Sclerotium gum | 1.8 |
| Water | qs 100 |

It is observed that composition B3 of the process according to the invention is homogeneous and forms a translucent gel at T0, and after 2 months at room temperature or at 45° C.

Composition A2 was mixed, respectively, with 1 times its weight of oxidizing composition B3.

Easy mixing of the compositions and the production of a homogeneous, translucent mixture are observed. The mixtures thus obtained were applied to locks of natural hair containing 90% white hairs.

The "mixture/lock" bath ratio is, respectively, 10/1 (g/g).

The mixture distributes easily and uniformly over the hair.

The working qualities are good: good wetting/glidant nature, good ease of application, good adhesion to the roots, good consistency on the head, good ease of extending the length of the fiber locks.

The leave-on time is 30 minutes, on a hotplate set at 27° C. On conclusion of the leave-on time, the locks are rinsed and then dried under a drying hood at 40° C.

The hair is then rinsed easily, and then washed with a standard shampoo and dried.

The color of the locks was evaluated in the CIE L*a*b* system, using a Datacolor Spectraflash SF600X spectrocolorimeter.

|  | L* |
|---|---|
| Mixture of compositions A2 and B3 | 21.48 |

Intense coloring of the keratin fibers is obtained.

The invention claimed is:

1. A method for dyeing keratin fibers, comprising applying to the keratin fibers:
   a) a dye composition (A) comprising:
      at least one oxidation dye;
      at least one scleroglucan gum present in a total amount of greater than or equal to 0.5% by weight, relative to the total weight of the dye composition (A); and
      at least one alkaline agent; and
   b) an oxidizing composition (B) comprising:
      at least one chemical oxidizing agent; and
      at least one scleroglucan gum;
   wherein the oxidizing composition (B) is extemporaneously mixed with the dye composition (A) just before use.

2. The method of claim 1, wherein the at least one scleroglucan gum is present in an amount ranging from 0.5% to 10% by weight, relative to the total weight of the dye composition (A).

3. The method of claim 1, wherein the at least one scleroglucan gum is present in an amount ranging from 0.5% to 2% by weight, relative to the total weight of the dye composition (A).

4. The method of claim 1, wherein the at least one oxidation dye (A) is chosen from benzene-based oxidation bases, or salts thereof; wherein the at least one oxidation dye (A) is optionally combined with at least one coupler chosen from meta-phenylenediamines, meta-aminophenols, meta-diphenols, naphthalene-based couplers, heterocyclic couplers, salts thereof, or mixtures thereof.

5. The method of claim 1, wherein the at least one oxidation dye (A) is chosen from para-phenylenediamines, bis(phenyl)alkylenediamines, para-aminophenols, ortho-aminophenols, heterocyclic bases, salts thereof, or mixtures thereof.

6. The method of claim 1, wherein the at least one alkaline agent is present in a total amount ranging from 1% to 20% by weight, relative to the total weight of the dye composition (A).

7. The method of claim 1, wherein the at least one alkaline agent is chosen from mineral alkaline agents, organic alkaline agents, or mixtures thereof.

8. The method of claim 1, wherein the at least one alkaline agent comprises at least one mineral alkaline agent and at least one organic alkaline agent.

9. The method of claim 7, wherein the mineral alkaline agents are chosen from aqueous ammonia, ammonia precursors, alkali metal silicates, alkaline-earth metal silicates, phosphates, carbonates, bicarbonates, sodium or potassium hydroxide, or mixtures thereof.

10. The method of claim 1, wherein the at least one alkaline agent is chosen from aqueous ammonia, alkali metal metasilicates, alkaline-earth metal metasilicates, alkanolamines, amino acids, or mixtures thereof.

11. The method of claim 1, wherein the dye composition (A) further comprises at least one surfactant chosen from cationic surfactants, nonionic surfactants, or mixtures thereof; wherein the at least one surfactant is present in a total amount ranging from 0.01% to 20% by weight, relative to the total weight of the dye composition (A).

12. The method of claim 11, wherein the at least one surfactant is nonionic chosen from:
   saturated or unsaturated, linear or branched, oxyethylenated fatty alcohols including at least one $C_8$ to $C_{40}$, and comprising from 1 to 100 mol of ethylene oxide;
   alkylpolyglycosides; or
   mixtures thereof.

13. The method of claim 1, wherein the dye composition (A) further comprises at least one associative polymer; wherein the at least one associative polymer is present in a total amount ranging from 0.01% and 10% by weight, relative to the total weight of the composition of the dye composition (A).

14. The method of claim 13, wherein the at least one associative polymer is nonionic.

15. The method of claim 13, wherein the at least one nonionic associative polymer is chosen from celluloses modified with groups including at least one fatty chain.

16. The method of claim 1, wherein the dye composition (A) further comprises at least one cationic polymer chosen from:
   (1) doalkyldialkylammonium homopolymers; and/or
   (2) cationic polymers that are constituted of repeating units corresponding to the formula (IV):

$$\begin{array}{c} R_1 \quad\quad\quad R_3 \\ | \quad\quad\quad\quad | \\ -\!\!\!-\!\!\!\mathrm{N}^+\!\!-\!(CH_2)_n\!-\!\mathrm{N}^+\!\!-\!(CH_2)_p\!-\!\!\!-\!\!\!- \\ | \quad\quad\quad\quad | \\ R_2 \;\; X^- \quad R_4 \;\; X^- \end{array} \quad (IV)$$

wherein in formula (IV), $R_1$, $R_2$, $R_3$ and $R_4$, which may be identical or different, are chosen from an alkyl or a hydroxyalkyl radical containing from 1 to 4 carbon atoms, n and p are integers ranging from 2 to 20, and X— is an anion derived from a mineral or organic acid.

17. The method of claim 1, wherein the at least one scleroglucan gum is present in an amount ranging from 0.5% to 10% by weight, relative to the total weight of the oxidizing composition (B).

18. The method of claim 1, wherein the at least one chemical oxidizing agent is chosen from hydrogen peroxide and/or at least one system generating hydrogen peroxide.

19. A multi-compartment device comprising:
a first compartment containing a dye composition (A); and
a second compartment containing an oxidizing composition (B);
wherein:
the dye compositions (A) comprises:
   at least one oxidation dye;
   at least one scleroglucan gum present in a total amount of greater than or equal to 0.5% by weight, relative to the total weight of the dye composition (A); and
   at least one alkaline agent; and
the oxidizing composition (B) comprises:
   at least one chemical oxidizing agent; and
   at least one scleroglucan gum.

20. The multi-compartment device of claim 19, wherein the device is in the form of an aerosol device.

* * * * *